(12) United States Patent
Turchetta et al.

(10) Patent No.: US 8,232,392 B2
(45) Date of Patent: Jul. 31, 2012

(54) PROCESS FOR PREPARING TEMOZOLOMIDE

(75) Inventors: Stefano Turchetta, Patrica (IT);
Lorenzo De Ferra, Patrica (IT);
Maurizio Zenoni, Patrica (IT); Mauro Anibaldi, Patrica (IT)

(73) Assignee: Chemi S.p.A., Cinisello Balsamo (MI) (IT)

( * ) Notice: Subject to any disclaimer, the term of this patent is extended or adjusted under 35 U.S.C. 154(b) by 363 days.

(21) Appl. No.: 12/461,049

(22) Filed: Jul. 30, 2009

(65) Prior Publication Data

US 2010/0036121 A1 Feb. 11, 2010

(30) Foreign Application Priority Data

Aug. 7, 2008 (EP) .................................... 08425547

(51) Int. Cl.
C07D 487/04 (2006.01)
C07D 233/66 (2006.01)

(52) U.S. Cl. ..................................... 544/179; 548/326.5
(58) Field of Classification Search .................. 544/179; 548/326.5
See application file for complete search history.

(56) References Cited

U.S. PATENT DOCUMENTS

| | | | | | |
|---|---|---|---|---|---|
| 6,844,434 | B2 * | 1/2005 | Kuo | ............................ | 544/179 |
| 7,087,751 | B2 * | 8/2006 | Kuo et al. | ..................... | 544/179 |
| 7,446,209 | B2 * | 11/2008 | Kuo et al. | .................. | 548/326.5 |
| 7,737,284 | B2 * | 6/2010 | Kuo et al. | .................. | 548/326.5 |

* cited by examiner

*Primary Examiner* — Venkataraman Balasubramanian
(74) *Attorney, Agent, or Firm* — Lucas & Mercanti, LLP

(57) ABSTRACT

Described is a new process for producing temozolomide, comprising the reaction between 5-aminoimidazole-4-carboxamide and N-succinimidyl-N'-methyl carbamate and the subsequent reaction of the thus obtained carbamoyl 5-aminoimidazole-4-carboxamide with sodium nitrite. Temozolomide is then purified by chromatography on adsorbent polymeric resin and subsequent crystallization from water and acetone.

31 Claims, No Drawings

PROCESS FOR PREPARING TEMOZOLOMIDE

A new method for preparing a cytotoxic active substance having a low environmental impact and a high safety profile is described in the present document.

Temozolomide or 3,4-dihydro-3-methyl-4-oxoimidazo[5,1-d]-1,2,3,5-tetrazine-8-carboxamide is an active substance with antineoplastic activity, widely used in the therapy of brain tumours.

Several synthetic routes for the preparation of Temozolomide are reported in the literature. U.S. Pat. No. 5,260,291 reports a synthesis starting from 5-aminoimidazole-4-carboxamide, effecting a diazotization with sodium nitrite and acids in order to obtain a diazonium salt intermediate which can be isolated and which is then treated with methyl isocyanate to derive Temozolomide.

This synthesis method is reported in scheme 1.

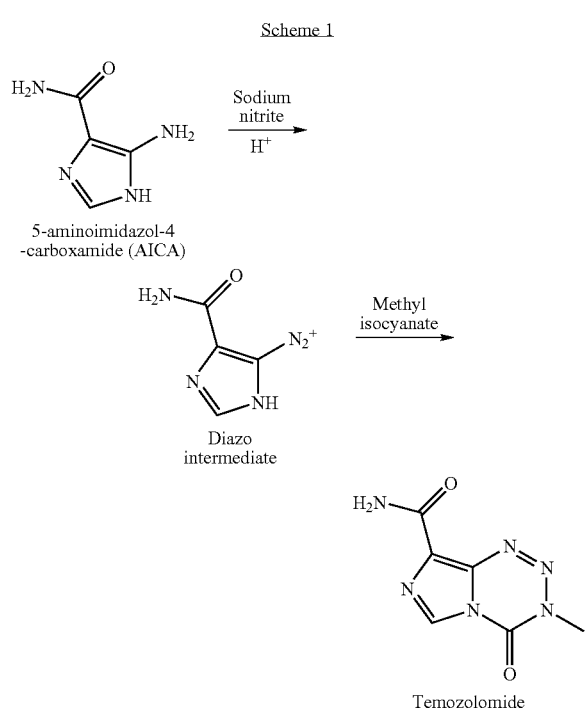

Such synthesis suffers from two crucial problems: the use of a potentially explosive intermediate and the use of a highly toxic and explosive substance in admixture with air, such as methyl isocyanate.

U.S. Pat. No. 6,844,434 describes a preparation of Temozolomide through a modified route, starting again from 5-aminoimidazole-4-carboxamide (indicated above as AICA), proceeding through a hydrazine intermediate which is then oxidized to temozolomide. Scheme 2 summarizes the synthesis method reported in this patent.

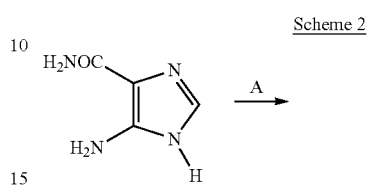

A = 4-nitrophenyl chloroformate/TEA/DMC
B = methylhydrazine/DMF
C = Bu$_4$NI/H$_5$IO$_6$/THF/acetonitrile The main disadvantage of this synthesis resides in the high number of synthetic steps and in the use of methyl hydrazine which is a potential carcinogen. U.S. Pat. No. 7,087,751 instead describes a synthesis of temozolomide, wherein the heterocyclic portion of the molecule is constructed so as to have a nitrogen-protected carboxamide group, which does not subsequently interfere with the cyclization to Temozolomide.

This synthesis method is reported in scheme 3.

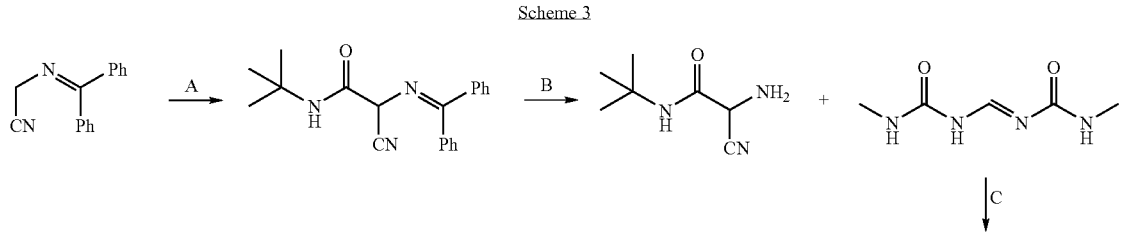

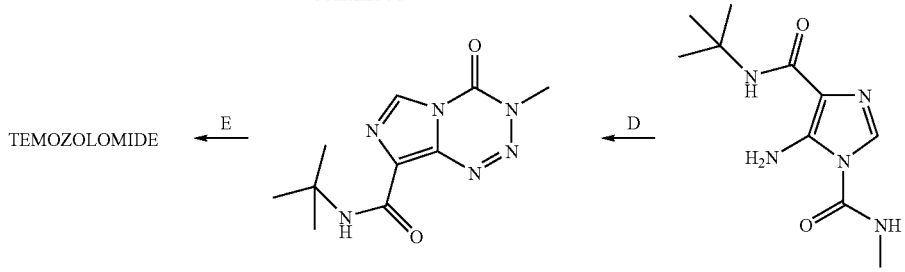

A = t-BuO⁻/t-BuNCO
B = HCl/EtOAc
C = CH₂Cl₂/CH₃COOH
D = NaNO₂/AcOH, LiCl, H₂O
E = H₂SO₄ conc.

This synthesis consists of a high number of synthetic steps, it makes use of a dangerous reactant such as t-butylisocyanate and has a low overall yield.

US2006/0183898 reports the synthesis of temozolomide carried out by hydrolysis of the corresponding cyano-derivative. The cyano-derivative of Temozolomide is obtained by application of the methods described in J. Org. Chem. Vol. 62, n. 21, 7288-7294 (1997). The disadvantages of this synthesis can be identified in the need of using methyl isocyanate for the preparation of the temozolomide cyano-derivative and in the low overall yield of the process starting from commercially available raw materials.

The synthesis described in this patent application is outlined in scheme 4.

Scheme 4

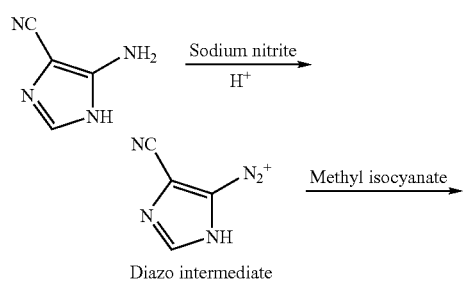

-continued

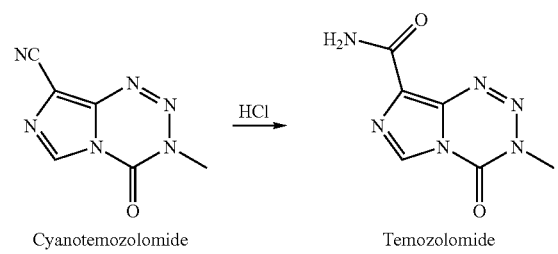

Cyanotemozolomide     Temozolomide

US2007/0225496 instead reports a variant of the method described in U.S. Pat. No. 5,260,291, wherein methyl isocyanate is generated by pyrolysis of a commercially available solid precursor, diphenylmethylurea. The disadvantages of this synthesis are again the use of a highly toxic reactant such as methyl isocyanate, which, despite the fact that it is generated in situ, has to be conveyed as a gas to the synthesis reactor, and the use of the diazonium salt intermediate, which is comparatively instable and which can violently decompose.

The synthesis described in this patent application is exemplified in scheme 5.

Scheme 5

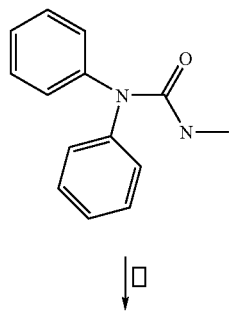

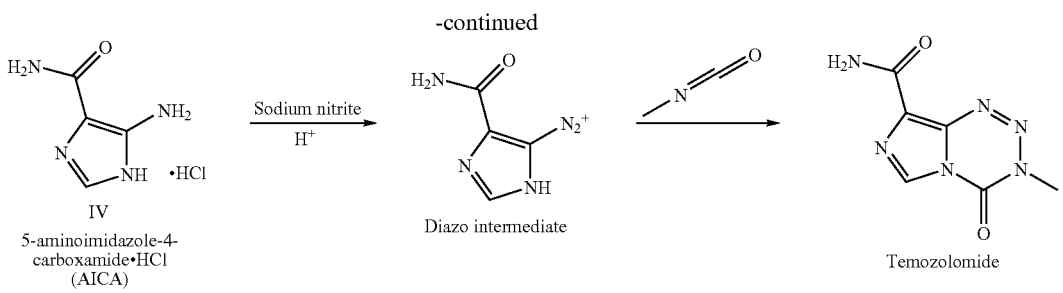

WO2008/038031 describes a synthesis of temozolomide, wherein the intermediate carbamoyl-AICA is diazotized and cyclized in the presence of a strong excess of lithium chloride and the resulting reaction mixture is extracted continuously with dichloromethane in order to recover temozolomide. The disadvantages of this synthesis method are the use of high amounts of Lithium chloride and the use of considerable amounts of dichloromethane, which makes the process unfavourable from an environmental point of view since it is not an environmentally friendly solvent. Scheme 6 reports the method described in the abovementioned patent application.

Scheme 6

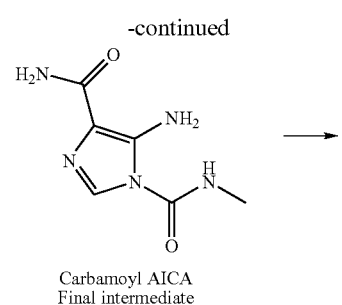

A) LiCl, Acetic acid/Water NaNO$_2$
B) continuous extraction with CH$_2$Cl$_2$

Essentially, there remains a need for a method that is safe with respect to the risks associated with dangerous intermediates (diazo-AICA) and reactants (methyl isocyanate) and has at the same time a low environmental impact (i.e. not using poorly eco-friendly solvents or large amounts of reactants which then need to be disposed of) in order to prepare the temozolomide.

The present invention relates to a method for the synthesis of temozolomide which uses water and moderate amounts of environmentally friendly organic solvents as process solvents, which does not use intermediates or reactants that are dangerous from the point of view of both toxicity and explosion hazard and leads to the production of pharmaceutical grade temozolomide in satisfactory yields. Such synthesis route is summarized in scheme 7.

Scheme 7

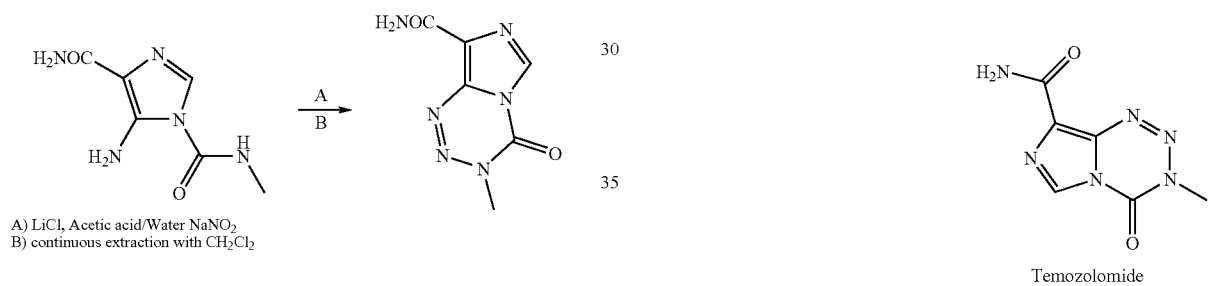

First Step. From AICA to Carbamoyl AICA

In the course of studies carried out to find a low risk synthesis of temozolomide, it was found that N-Succinimidyl-N'-methyl carbamate, a non-explosive and comparatively low-toxicity stable crystalline solid, is able to functionalize base AICA very effectively to give Carbamoyl AICA.

The adopted synthesis route and the structural formula of N-Succinimidyl-N'-methyl carbamate are summarized in scheme 8.

Scheme 8

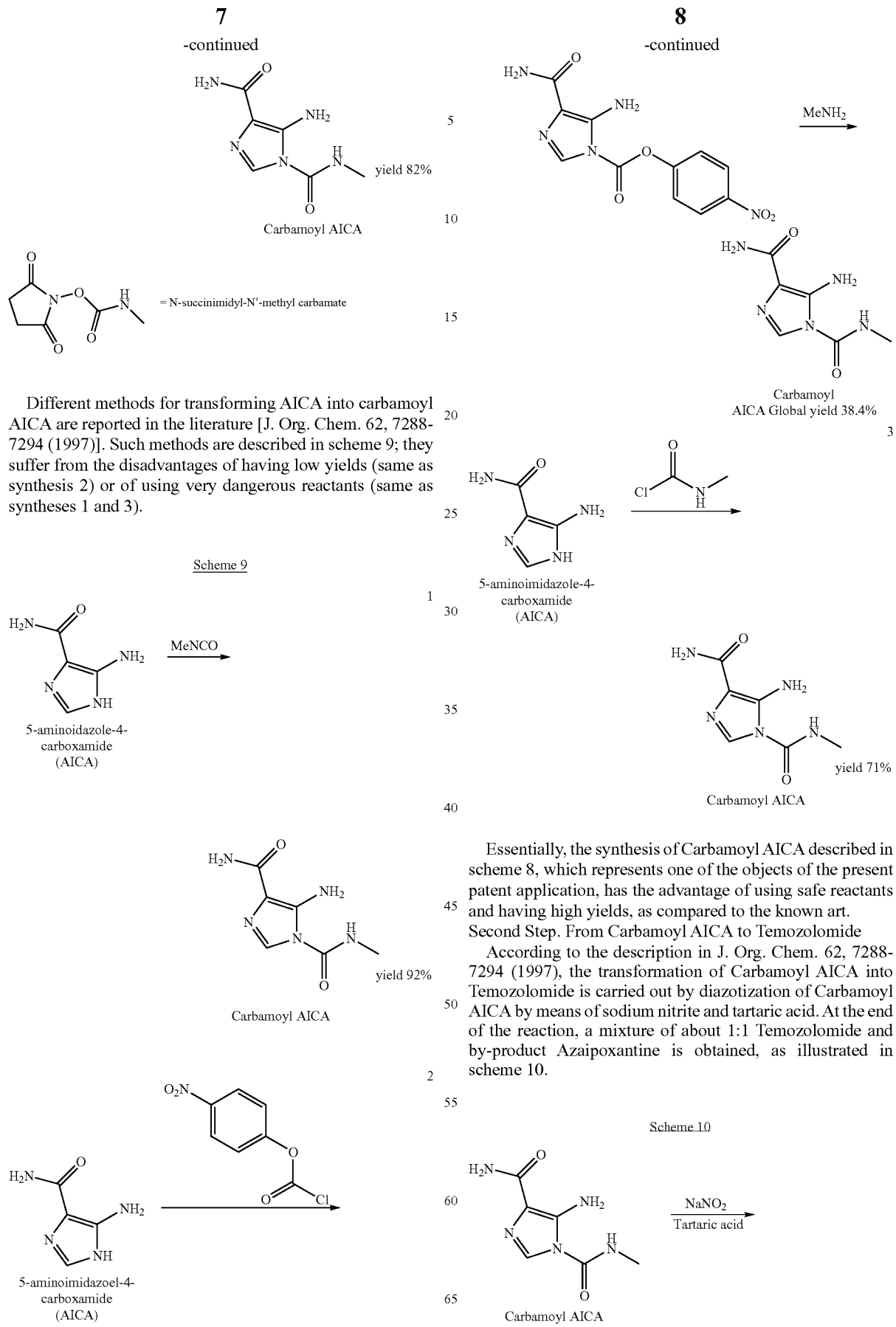

Different methods for transforming AICA into carbamoyl AICA are reported in the literature [J. Org. Chem. 62, 7288-7294 (1997)]. Such methods are described in scheme 9; they suffer from the disadvantages of having low yields (same as synthesis 2) or of using very dangerous reactants (same as syntheses 1 and 3).

Essentially, the synthesis of Carbamoyl AICA described in scheme 8, which represents one of the objects of the present patent application, has the advantage of using safe reactants and having high yields, as compared to the known art.

Second Step. From Carbamoyl AICA to Temozolomide

According to the description in J. Org. Chem. 62, 7288-7294 (1997), the transformation of Carbamoyl AICA into Temozolomide is carried out by diazotization of Carbamoyl AICA by means of sodium nitrite and tartaric acid. At the end of the reaction, a mixture of about 1:1 Temozolomide and by-product Azaipoxantine is obtained, as illustrated in scheme 10.

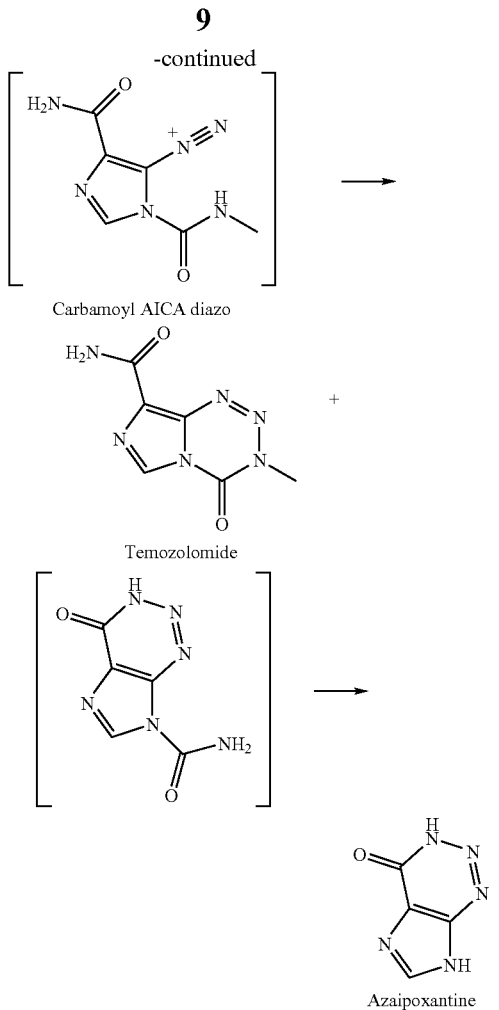

The formation of the two products is determined by the two-fold possibility of cyclizing the transient intermediate Carbamoyl AICA diazo, which can close the six-membered cycle both with the primary carbamoyl group (to give the intermediate indicated in square brackets which evolves to azaipoxantine), and the secondary carbamoyl group (to give temozolomide).

The technical problem to be solved is thus that of realizing an effective separation of the two products and a recovery of temozolomide having a quality suitable for pharmaceutical use.

Object of the present patent application is also an effective method for the purification of temozolomide from azaipoxantine and the consequent production of temozolomide having a suitable purity level for pharmaceutical use.

In fact, it was found that by passing the diazotization reaction mixture of carbamoyl AICA, mainly containing temozolomide and azaipoxantine, on a column filled with adsorbent polymer resin, it is possible to bring about an effective separation of azaipoxantine and temozolomide and to recover temozolomide from the column, the latter having sufficient purity to be recrystallized to temozolomide suitable for pharmaceutical use.

By purity suitable for pharmaceutical use it is intended a purity meeting the requirements dictated by the ICH (International Conference for Harmonization). Examples of adsorbent polymeric resins may be XAD 1600 (Rohm and Haas), XAD 1180 (Rohm and Haas), HP20L (Mitsubishi), HP 2055 (Mitsubishi), SP825 (Mitsubishi).

In the following examples, the process which is the object of the present patent application is described by way of example; these examples are not intended to limit the scope of protection of the same.

EXAMPLE 1

Synthesis of Carbamoyl AICA 200 g of base AICA as is (K. F. 11%) corresponding to 178 g of 100% base AICA and 1000 ml of acetonitrile are charged in a 2-liter reactor.

The mixture is stirred at room temperature (about 20° C.) and 267 g of N-Succinimidyl-N'-methyl carbamate and 191.7 g of diisopropylethylamine (DIPEA) are added to the suspension.

The temperature of the mixture is kept at 25±2° C. for 16 hours, then the mixture is cooled at 0÷5° C., held for an hour and the suspension is filtered on a Buchner, by washing with 2×200 ml of deionised water. 313.0 g of wet product are discharged, which is then dried on a rotavapor for 5 hours at 50° C. with vacuum line. 212 g of Carbamoyl AICA (96.9% HPLC purity) are obtained, with 0.13% K. F. 88% yield.

EXAMPLE 2

Preparation of Temozolomide

Following the method published in J. Org. Chem. 62, 7288-7294 (1997) on page 7293, second example of the first column, a reaction crude is generated starting from 18 g of Carbamoyl AICA, mainly containing Temozolomide and Azaipoxantine in approximately a 1:1 ratio.

An amount of 5% HCl sufficient to bring the pH to 2÷2.2 is added to this reaction mixture which is then charged in a 100 ml glass pre-column, charged with 60 ml of XAD 1600 resin, which is connected to a glass column filled with 600 ml of XAD 1600 resin. Both columns are previously washed and conditioned with a solution of water and HCl at a pH of 2÷2.2.

The elution is carried out at a flow rate between 0.5 and 2 BV/h, while controlling the eluate fractions by means of HPLC. Once the outflow of azaipoxantine from the column is completed (taking place before the outflow of temozolomide from the column), the pre-column is disconnected and the elution is continued with a mixture of water at pH 2÷2.2 for HCl and ethanol 90:10, while collecting the temozolomide-containing eluate.

The solution containing the reunited temozolomide-containing fractions is evaporated to obtain a residue, which is recrystallized by being refluxed after addition of a mixture made up of 240 ml of acetone and 80 ml of acidulated water at pH 2 with HCl. After cooling, the precipitated solid is filtered, washed with the 1:3 mixture of water-acetone, discharged from the filter and dried. 5.8 g of temozolomide are thereby obtained, with HPLC purity >99.9% and single impurity lower than 0.10% (30% yield).

The invention claimed is:

1. Process for producing temozolomide comprising the following steps:
    (a) reacting 5-aminoimidazole-4-carboxamide and N-succinimidyl-N'-methyl carbamate in the presence of a tertiary amine to give carbamoyl 5-aminoimidazole-4-carboxamide;
    (b) reacting the carbamoyl 5-aminoimidazole-4-carboxamide thus obtained with an alkali or alkaline-earth nitrite to give temozolomide.

2. Process according to claim 1, wherein step (a) is carried out in an aprotic polar organic solvent.

3. Process according to claim 2 wherein said aprotic polar organic solvent is acetonitrile.

4. Process according to claim 2, wherein the volume/weight ratio between said aprotic polar organic solvent and 5-aminoimidazole-4-carboxamide is between 2 and 8.

5. Process according to claim 1, wherein the weight ratio between N-succimidyl-N'-methyl carbamate and 5-aminoimidazole-4-carboxamide is between 1 and 1.5.

6. Process according to claim 1, wherein step (a) is carried out in the presence of an alkyl amine.

7. Process according to claim 6, wherein the weight ratio between said alkyl amine and 5-aminoimidazole-4-carboxamide is between 0.8 and 1.2.

8. Process according to claim 1, wherein said alkali nitrite is sodium nitrite.

9. Process according to claim 1, wherein step (b) is carried out in the presence of an acid.

10. Process according to claim 9, wherein said acid is an inorganic acid.

11. Process according to claim 1, wherein the temozolomide thus obtained is purified by means of chromatography on adsorbent polymeric resin and subsequent crystallization.

12. Process for preparing the carbamoyl 5-aminoimidazole-4-carboxamide of claim 1 comprising
reacting 5-aminoimidazole-4-carboxamide and N-succinimidyl-N'-methyl carbamate in the presence of a tertiary amine.

13. Process according to claim 12, carried out in an aprotic polar organic solvent.

14. Process according to claim 13, wherein said aprotic polar organic solvent is acetonitrile.

15. Process according to claim 13, wherein the volume/weight ratio between said aprotic polar organic solvent and 5-aminoimidazole-4-carboxamide is between 2 and 8.

16. Process according to claim 12, wherein the weight ratio between N-succinimidyl-N'-methyl carbamate and 5-aminoimidazole-4-carboxamide is between 1 and 1.5.

17. Process according to claim 12, wherein it is carried out in the presence of an alkyl amine.

18. Process according to claim 17, wherein the weight ratio between said alkyl amine and 5-aminoimidazole-4-carboxamide is between 0.8 and 1.2.

19. Process steps involved in the purification of temozolomide by means of chromatography on adsorbent polymeric resin.

20. Process steps according, to claim 19, wherein said adsorbent polymeric resin is chose from XAD 1600 (Rohm and Haas), XAD 1180 (Rohm and Haas), HP20L (Mitsubishi), HP2055 (Mitsubishi), SP825 (Mitsubishi).

21. Process steps according to claim 19, wherein, after said chromatography, temozolomide is crystallized from a mixture of water and an aprotic polar organic solvent.

22. Process steps according to claim 21, wherein said aprotic polar organic solvent is acetone.

23. Process steps according to claim 21, wherein the volume ratio between said aprotic polar organic solvent and water is between 2 and 4.

24. Process according to claim 4, wherein the volume/weight ratio is between 4 and 6.

25. Process according to claim 4, wherein the volume/weight ratio is about 5.

26. Process according to claim 5, wherein the weight ratio is between 1.2 and 1.4.

27. Process according to claim 6, wherein step (a) is carried out in the presence of a trialkyl amine.

28. Process according to claim 6, wherein step (a) is carried out in the presence of diisopropylethylamine.

29. Process according to claim 7, wherein the weight ratio is between 0.9 and 1.

30. Process according to claim 10, wherein said acid is hydrochloric acid.

31. Process according to claim 23, wherein the volume ratio between said aprotic polar organic solvent and water is between 2.5 and 3.5.

* * * * *